United States Patent
Faraggi

(10) Patent No.: US 11,160,536 B2
(45) Date of Patent: Nov. 2, 2021

(54) ULTRASOUND METHOD AND ULTRASOUND SYSTEM FOR REAL TIME AUTOMATIC SETTING OF PARAMETERS FOR DOPPLER IMAGING MODES

(71) Applicant: ESAOTE SpA, Genoa (IT)

(72) Inventor: Massimo Faraggi, Genoa (IT)

(73) Assignee: Esaote S.p.A., Genoa (IT)

( * ) Notice: Subject to any disclaimer, the term of this patent is extended or adjusted under 35 U.S.C. 154(b) by 395 days.

(21) Appl. No.: 16/136,836

(22) Filed: Sep. 20, 2018

(65) Prior Publication Data

US 2019/0099161 A1  Apr. 4, 2019

(30) Foreign Application Priority Data

Oct. 3, 2017 (EP) .................................. 17194484

(51) Int. Cl.
*A61B 8/08* (2006.01)
*G06T 7/155* (2017.01)
(Continued)

(52) U.S. Cl.
CPC .............. *A61B 8/5207* (2013.01); *A61B 8/06* (2013.01); *A61B 8/0891* (2013.01); *A61B 8/488* (2013.01);
(Continued)

(58) Field of Classification Search
CPC ..... A61B 8/5207; A61B 8/488; A61B 8/0891; A61B 8/06; A61B 8/469; A61B 8/461;
(Continued)

(56) References Cited

U.S. PATENT DOCUMENTS 5,365,929 A  11/1994  Peterson
5,690,116 A  11/1997  Goujon
(Continued)

FOREIGN PATENT DOCUMENTS

| EP | 1152364 A2 | * 11/2001 | ............... A61B 8/06 |
| EP | 1152364 A2 | 11/2001 | |
| EP | 2848200 A1 | 3/2015 | |

OTHER PUBLICATIONS

N.A.: Filtering an Image, Jun. 16, 2005, XP055461152, Retrieved from Internet: URL:http://northstar-www.dartmouth.edu/doc/idl/html_6.2/Filtering_an_Imagehvr.html, retrieved on Mar. 20, 2018, "Section Directional Filtering".
(Continued)

*Primary Examiner* — Christopher Koharski
*Assistant Examiner* — Kaitlyn E Selmer
(74) *Attorney, Agent, or Firm* — Dickinson Wright PLLC

(57) ABSTRACT

To lessen the examination time in an Ultrasound system in a vascular Exam routine, it is desirable to: automatically position in the best way Color Doppler ROI and/or Sample Gate; select the best Color Doppler/Beamline Steering angle; and set the Doppler Correction angle. An algorithm is provided that is able to process in real time the Doppler Signal to identify the Doppler Area where the most significant flow is present, and then it analyzes the 'Shape' of such Color Doppler Area identifying the Position and direction of the "main" Flow. The vascular Examination routine can therefore be made easier and faster.

21 Claims, 8 Drawing Sheets

(51) Int. Cl.
*G01S 15/89* (2006.01)
*G06T 7/11* (2017.01)
*A61B 8/06* (2006.01)
*A61B 8/00* (2006.01)
*G01S 7/52* (2006.01)

(52) U.S. Cl.
CPC ...... *G01S 7/52063* (2013.01); *G01S 15/8979* (2013.01); *G01S 15/8988* (2013.01); *G06T 7/11* (2017.01); *G06T 7/155* (2017.01); *A61B 8/461* (2013.01); *A61B 8/469* (2013.01); *G01S 7/52046* (2013.01); *G06T 2207/10132* (2013.01)

(58) Field of Classification Search
CPC ....... A61B 8/54; A61B 8/585; G01S 7/52063; G01S 15/8979; G01S 15/8988; G01S 7/52046; G06T 7/155; G06T 7/11; G06T 2207/10132
See application file for complete search history.

(56) References Cited

U.S. PATENT DOCUMENTS

| | | | |
|---|---|---|---|
| 6,322,509 B1 | 11/2001 | Pan et al. | |
| 8,047,991 B2* | 11/2011 | Srinivasan | A61B 8/13 600/443 |
| 2004/0081340 A1* | 4/2004 | Hashimoto | G01S 7/52036 382/128 |
| 2007/0073153 A1* | 3/2007 | Tortoli | A61B 8/4483 600/454 |
| 2014/0221838 A1 | 8/2014 | Loupas et al. | |
| 2017/0156704 A1* | 6/2017 | Flynn | A61B 8/463 |

OTHER PUBLICATIONS

European Search Report dated Mar. 28, 2018, which issued in the corresponding EP Patent Application No. 17194484.6.

* cited by examiner

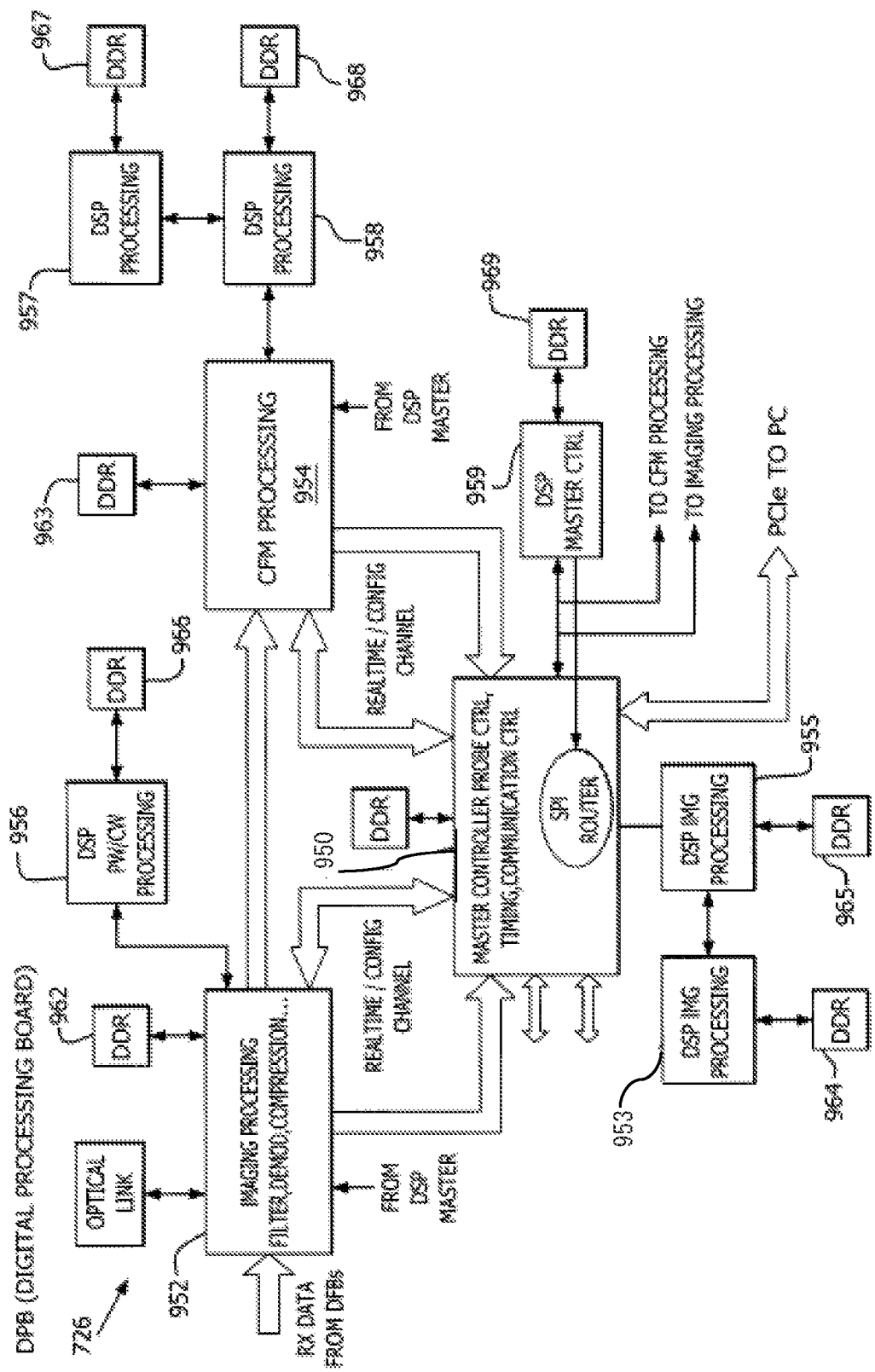

ULTRASOUND METHOD AND ULTRASOUND SYSTEM FOR REAL TIME AUTOMATIC SETTING OF PARAMETERS FOR DOPPLER IMAGING MODES

BACKGROUND OF THE INVENTION

The present disclosure relates to an ultrasound method and to an ultrasound system both for real time automatic setting of parameters for color Doppler imaging mode.

Ultrasound imaging systems are operable alternatively or in combination in several imaging modes which furnishes different views and thus different features of the imaged object. Among the different modes, the most common modes are:

B mode for tissue imaging,
Doppler modes for flow analysis and imaging.

Typical Doppler modes include Power Doppler mode used for both tissue motion and flow imaging, Color Flow Doppler mode for qualitative flow imaging, and Spectral Doppler mode for flow quantification.

Doppler image data can be related to mono-dimensional images, bi-dimensional images (2D) and three-dimensional images (3D). Also the method and the system described herein can be used for acquiring mono-dimensional, bi-dimensional and three-dimensional images.

During vascular examinations by means of an ultrasound imaging system, ColorFlow Doppler imaging mode is frequently used for examining the anatomical conditions of the blood vessels and provide a diagnosis about the presence of a vascular diseases.

The vascular examination routine includes to carry out operations for positioning in the best way the Color Doppler region of interest (ROI) and/or the Doppler Sample Gate and/or to select the best Color Doppler-Beamline Steering angle and/or to set the Doppler Correction angle. Carrying out these operations manually is time consuming and increases the examination time and the costs. Currently different techniques are available for carrying out the above operations in real time and in an automatic way.

The state of the art comprises different methods for automatic settings of the best positioning of the Color Doppler ROI and/or the Doppler Sample Gate and/or of the best Color Doppler-Beamline Steering angle and/or of the Doppler Correction angle but these known methods does not operate in a fully automatic way and in true real time, particularly when following the change of the scanned target (e.g. moving the probe).

US 2014/0221838 describes an ultrasound system which automates the color box placement, Doppler sample volume placement, angle correction, and beam steering angle using vessel segmentation and flow image analysis.

U.S. Pat. No. 6,322,509 describes a method for automatically adjusting the Doppler sample gate position and size settings based on the vessel image data. Using an object search technique based solely on geometric and morphological information in a binarized vessel image obtained from either B-mode or color flow image data a vessel segment is searched. The morphologically best or nearest vessel segment within a target search region in a two-dimensional image is found. The sample gate is placed at or near the center of the targeted vessel segment and the size of the sample gate is adjusted in relation to the vessel size. The best available steering angle minimizing the Doppler angle is selected.

In U.S. Pat. No. 8,047,991 a direction and/or an orientation are automatically identified in ultrasound image by using region shrinking process or by using locations associated with flow or tissue structure.

In U.S. Pat. No. 5,690,116 an histogram based method is discloses. According to this document, an automatic measurement is made of the angle enclosed by the direction of ultrasonic echographic beam and the axis of a vessel, defined as Doppler angle, in an echographic image on the basis of prior designation of an initial point Pi in the vessel. A first isotropic tracing of rays starting from the initial point Pi is used to produce a histogram of the grey levels of the points of the rays. An algorithm is then applied to the histogram in order to classify the grey levels of selected points. A second tracing of rays is made which is restricted to the walls of the vessel and provides information for determining the slope of a regression line is and the calculation of the Doppler angle.

There is a need for a method and system for real time automatic setting of parameters for color Doppler imaging mode and particularly automatic positioning in the best way the Color Doppler ROI and/or the Sample Gate and/or automatically selecting the best Color Doppler/Beamline Steering angle and/or automatically setting the Doppler Correction angle, not only in response of a user action but also in adapting to a change of the scanned target (e.g. moving the probe) which method and which system provides for a faster and easier vascular examination routine.

SUMMARY

It is an object to provide a method for automatic measurement of the Doppler angle of a blood vessel in an echographic image, starting from a designated point.

It is another object to provide a method for automatic measurement of the Doppler angle which is exact and fast.

A further object consists in providing an ultrasound system configured for carrying out the above measuring method.

According to a first aspect a method for real time automatic setting of parameters for color Doppler imaging mode is provided comprising the following steps:

transmitting ultrasound beams in a target body and receiving the reflected beam from the said target body;

extracting Color Doppler signals from the said reflected beams;

processing the Color Doppler signals to identify an area where the Color Doppler signals indicate that a flow is present and processing the Color Doppler signals relating to the said area for automatically determining one or more of the following parameter settings:

best positioning of the Color Doppler ROI and/or of the Doppler sample Gate, determining and applying the best Color Doppler beam steering angle, setting the Doppler correction angle, processing the said Color Doppler Signals comprises:
analysing the shape of the identified Color Doppler area by processing the corresponding Color Doppler signals for determining:

a) the position of a flow having the most significant intensity;

b) the direction of the flow at the position as determined in a);

determining the best position of the Color Doppler ROI and/or of the Doppler sample gate as a function of the said position of the flow and positioning the said Color Doppler ROI and/or sample gate on that position;

determining the steering angle of the transmit beams and/or the Doppler correction angle as a function of the direction of the flow.

According to an embodiment, the operation of analysing the shape of the identified Color Doppler area is based on morphological features of the flow determined from the Color Doppler flow signals.

In a further embodiment, analysing the shape of the identified Color Doppler area comprises creating a virtual Doppler image of the flow from the Color Flow signals.

According to an embodiment, determining the position of a flow having the most significant intensity comprises:
optionally sampling and/or filtering the virtual Doppler image;
calculating the maximum value of the pixels or voxels of the virtual Doppler image and selecting the position of the said pixel or voxel as the position of the flow.

In combination of one or more of the previously described embodiments in a further improvement determining the direction of the flow comprises:
applying four directional filters on the virtual Doppler image at the position of the pixels having the maximum value, the said directional filters being oriented respectively along one of four directions each being rotated of 45° with respect to an adjacent direction
combining the output of the said four directional filters to obtain a vector;
determining the flow direction as a function of the direction of said vector.

According to embodiments herein, determining the direction of the flow comprises:
applying four directional filters on the virtual image at the position of the pixels having the maximum value, the said directional filters being oriented respectively along the following directions defined by the axis passing through the directions of a goniometer centred on the centre position of the flow according to the following notation 0°-180°, 45°-215°, 90°-270° and 135°-315° the goniometer being aligned with the axis of a Cartesian system defining the two dimensions of the image with the 0°-180° axis and the 90°-270° axis;
combining the output of the said four directional filters forming a vector with orthogonal components x and y having the following values X=(output of the filter having direction 0°-180°)−(output of the filter having direction 90°-270°) and Y=(output of the filter having direction 45°-215°)−(output of the filter having direction 135°-315°);
determining the phase of the vector and calculating the flow direction angle as a function of the said phase.

According to an embodiment, the virtual Doppler images from which the directions are calculated are subsampled, particularly by a factor 2.

According to a further variant embodiment the virtual Doppler images are filtered by a smoothing filter.

According to an embodiment, the function for determining the flow direction is calculated as:

$$\text{DIRECTION} = \frac{1}{2}\text{atan}\left(\frac{Y}{X}\right)\frac{180}{\pi}$$

According to a further improvement, the normalized module Q of the vector can be calculated and used as factor of merit, or quality factor, of the estimation of the direction.

An embodiment provides the following function for calculating the normalized module Q of the vector:

$$Q = \frac{\sqrt{(F0 - F90)^2 + (F45 - F135)^2}}{\sqrt{(F0 + F90)^2 + (F45 + F135)^2}}$$

In which:
F0 is the output of the filter having direction 0°-180°;
F45 is the output of the filter having direction 45°-215°;
F90 is the output of the filter having direction 90°-270° and
F135 is the output of the filter having direction 135°-315°

According to an embodiment the method provides for the additional steps of:
Defining a threshold for the value of the said normalized module of the vector determined according to one or more of the embodiments described above;
calculating the said normalized module Q;
comparing the said calculated value for the normalized module with the threshold;
setting the best Color Doppler Beam-axis steering angle and the Doppler correction angle according to the flow directions calculated as the function of the phase of the same vector of which the normalized module is calculated if this calculated value of the said normalized module is above the threshold.

According to a further aspect an ultrasound imaging system is provided comprising:
an ultrasonic probe including a transducer array which probe transmits ultrasound beams in a target region where a flow is present and which receives the echo signals reflected by the said target region;
a beamformer which controls the directions in which the ultrasound beams are transmitted by the probe;
a Doppler processor producing Doppler signals from the echo signals;
an image processor producing Doppler images of the flows in target region;
a Color Doppler ROI and/or Doppler sample gate positioning processor for automatically positioning the ROI and/or a sample gate in the best position relatively to the imaged flow;
a Steering angle and/or Doppler correction angle processor for automatically determining the best steering angle and setting the corresponding best correction angle of the ultrasound beams propagation directions;
the said Color Doppler ROI and/or Doppler sample gate positioning processor and the steering angle and/or Doppler correction angle processor are configured to processing the color Doppler flow signals and determining data relating to morphological features of the flow and calculating the best position for the Color Doppler ROI and/or the Doppler sample gate and the Steering angle and/or the Doppler correction angle as a function of the said data on morphological features.

According to an embodiment, the positioning processor is provided in combination with a color Doppler image processing unit generating an image from the color Doppler signals and is configured to determine the maximum pixel value and the position of the corresponding pixel, the said color Doppler image processing unit comprises a ROI and or sample gate manager unit automatically positioning or centering the ROI and/or the sample gate at the position of said pixel having the maximum value.

According to still a further embodiment, the Steering angle and/or Doppler correction angle processor is provided in combination with a color Doppler image processing unit generating an image from the color Doppler signals and comprises a filter unit provided with four direction filters each oriented along one of four directions each being rotated of 45° with respect to an adjacent direction, The outputs of the four directional filters being connected to the Steering angle and/or Doppler correction angle processor being configured to calculate the flow direction and a factor of merit of the calculated direction.

According to an embodiment, the positioning processor comprises a sampling unit for subsampling the Color Doppler image and optionally a smoothing filter of the subsampled image.

According to an embodiment, the Steering angle and/or Doppler correction angle processor comprises a sampling unit for subsampling the Color Doppler image.

In a further embodiment the Steering angle and/or Doppler correction angle processor comprises a memory for saving a threshold value for the factor of merit and a comparator for comparing the calculated factor of merit with the threshold, the comparator output being read by the Steering angle and/or Doppler correction angle processor for determining whether the flow direction calculated can be used for determining the steering angle of the transmit beam and/or the Doppler correction angle.

According to an embodiment a program is loaded and executed by the Steering angle and/or Doppler correction angle processor the said program configuring the said processor for calculating the flow direction and the factor of merit as a function of the outputs of the four directional filters according to the following functions:

$$\text{DIRECTION} = \frac{1}{2}\text{atan}\left(\frac{Y}{X}\right)\frac{180}{\pi}$$

Where X and Y are the components of a vector determined by combining the output values of the four direction filters according to the following:
X=F0-F90 and Y=F45-F135
In which
F0 is the output of the filter having direction 0°-180°;
F45 is the output of the filter having direction 45°-215°;
F90 is the output of the filter having direction 90°-270° and
F135 is the output of the filter having direction 135°-315°
And the quality factor corresponding to the normalized modulus of the said vector having the components X and Y defined above, where:

$$Q = \frac{\sqrt{(F0 - F90)^2 + (F45 - F135)^2}}{\sqrt{(F0 + F90)^2 + (F45 + F135)^2}}$$

And in which F0, F45, F90, F135 are according to the above definition.

As it appears from the above describe embodiments, determining the best position of the Color Doppler flow and/or of the sample gate and the best steering angle of the transmit beam and the corresponding Doppler correction angle is a very simple operation which can be carried out quickly. Thus in using the method and the system according to the above embodiments, the determination of the best ROI position and/or best sample gate position and of the best steering angle and Doppler correction angle can be carried out very quickly and in real time without introducing any delay which slows down the vascular examination routine and rendering easier and faster this routine.

Furthermore, the simplicity of the calculations to be carried out and in general of the entire automatic process allows to automatically follow any change in relation to the scanned target such as for example when moving the probe.

From the point of view of the implementation of the method in an ultrasound system, since the process consists essentially in a specific processing of signals which are in any case received and produced by the existing and traditional units of an ultrasound scanner, the Steering angle and/or Doppler correction angle processor and the positioning processor can be generic processors already provided in an ultrasound system and in which a program is loaded and executed, in the said program the steps of the method according to one or more of the described embodiments being coded in the form of instructions which configures the generic processor and the peripheral connected to it for carrying out the functions of operative units needed for executing the steps of the method.

According to a further aspect a readable medium is provided in which the instructions are coded for configuring a generic processor and optionally the peripherals connected to it in such a way that the processor and one or more of the said peripherals carry out the functions of operating units needed for executing the method, the said medium being readable by a reader unit or being stably installed as a peripheral of the processor. Non-exhaustive examples of such mediums are CD-ROM, CD-RAM, DVD-ROM, DVD-RAM, memory cards, USB memory sticks, portable hard disks, internal hard disks and other similar devices.

BRIEF DESCRIPTION OF THE DRAWINGS

FIG. 9 illustrates a block diagram of the digital processing board.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1:
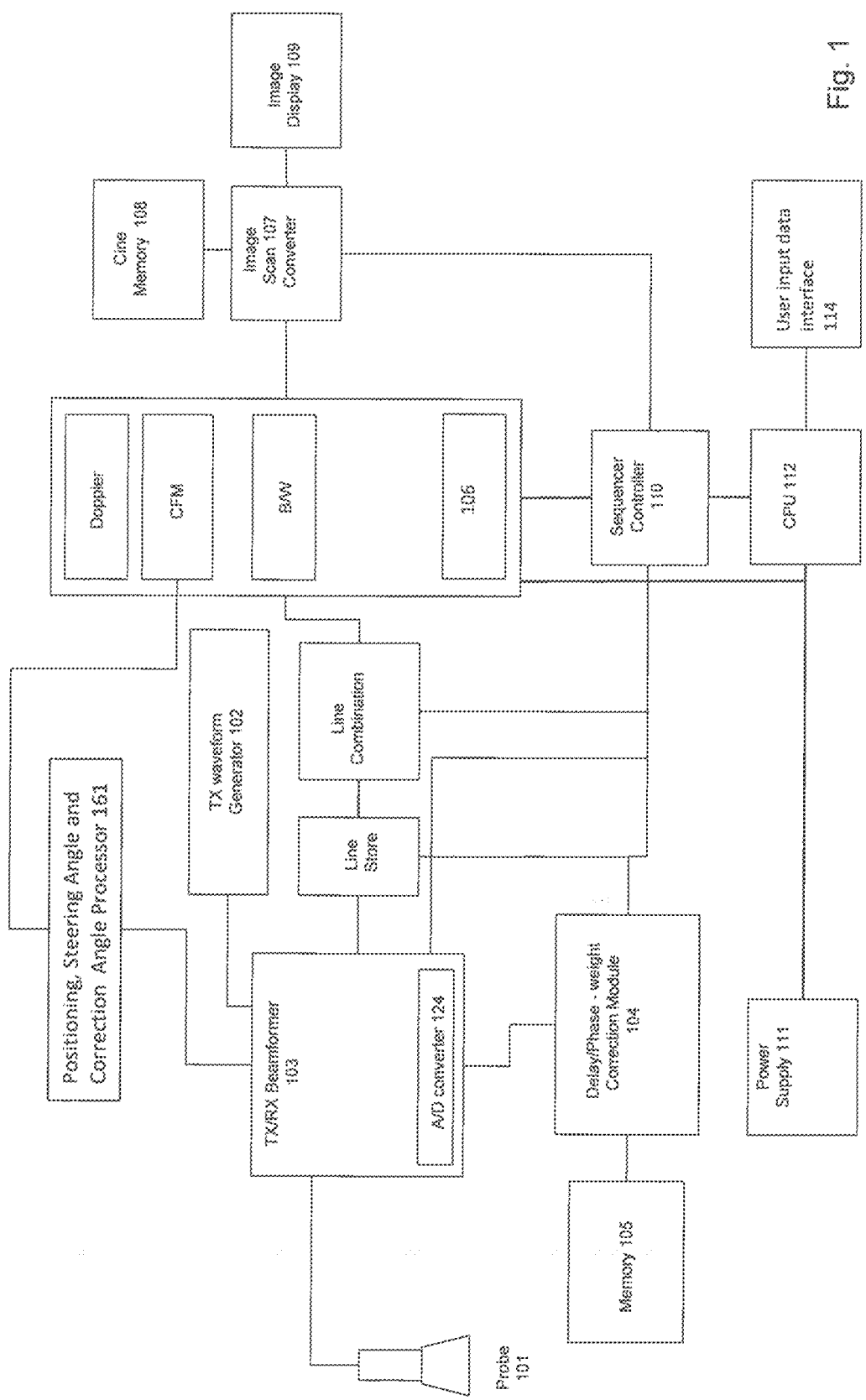
FIG. 1 illustrates a block diagram of an ultrasound system according to an embodiment.

FIG. 1 illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally, or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The TX and RX portions of the beamformer may be implemented together or separately. The beamformer 103 supplies transmit signals to the probe 101 and performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 103 performs beamforming of the transmit beams in order to focalize the transmit beams progressively along different adjacent lines of sight covering the entire ROI. The beamformer performs also beamforming upon received echo signals to form beamformed echo signals in connection to pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

The beamformer 103 includes (or is coupled to) an A/D converter 124 that digitizes the receive signals at a selected sampling rate. The digitization process may be performed before or after the summing operation that produces the coherent receive signals.

Optionally, a dedicated sequencer/timing controller 110 may be programmed to manage acquisition timing which can be generalized as a sequence of firings aimed at selected reflection points/targets in the ROI. The sequence controller 110 manages operation of the TX/RX beamformer 103 in connection with transmitting ultrasound beams and measuring image pixels at individual line of sight (LOS) locations along the lines of sight. The sequence controller 110 also manages collection of receive signals.

One or more processors 106 perform various processing operations as described herein.

In accordance with embodiments herein the beamformer 103 includes an output that is configured to be coupled to an ultrasound probe 101 and sends signals to the transducer elements of the probe 101.

According to an embodiment herein the sequencer 110 controls the beamformer in order to generate and transmit a plurality of transmit beams which are focalized in such a way as to show an aperture or a beam width encompassing a certain number of line of sights or of receive lines. The transmit beams of the said plurality being progressively laterally shifted along the array of transducer elements of the probe and thus along the ROI for scanning the entire ROI. A certain line of sight or a certain receive line will be encompassed by a certain number of different transmit beams of the said plurality as long as the said line of sight position or the said receive line position falls within the aperture of the said transmit beams or within the width of the said transmit beams. Thus, for a reflecting point on a certain receive line or line of sight having a certain line position within the ROI and relatively to the transducer array of the probe a certain number of receive signals contributions are received each one deriving from a different transmit beam whose center transmit line having different lateral shifts relatively to the said reflecting point and to the corresponding receive line.

The receive data relative to the echoes from the said reflecting point is a combination of the contributions of the receive signals from the said reflecting point deriving from the said certain number of transmit beams.

In accordance with embodiments herein, the beamformer 103 includes an input that is configured to be coupled to an ultrasound probe 101 and receive signals from transducers of the ultrasound probe 101. The memory 105 stores time delays to align contributions of reflection signals received by the transducers of the array of the probe 101 from the reflectors in the ROI. The memory 105 also stores phase corrections to correct phase differences of the receive signals contributions for each transducer element and deriving from each of the said certain number of differently laterally shifted transmit beams relatively to the receive line or line of sight on which the said reflector point is located.

A delay/phase correction (DPC) module 104 is coupled to the memory 105 and provides various delays and corrections to the beamformer 103. For example, the DPC module 104 directs the beamformer 103 to apply time delay and phase correction to the receive signals to form delayed receive signals. The beamformer 103 then sums, in a coherent manner, the delayed receive signals to obtain a coherent receive signal in connection with a reflection point or a reflection target.

Optionally, the memory 105 may store a common phase shift correction in connection with multiple channels. Different phase shift corrections may be stored in connection with various corresponding channels in the case of multiple receive signals that are received along a common receive line position but, due to a certain number of different transmit beams, each one having a laterally shifted transmit center line and an aperture or width encompassing the receive line position. The memory 105 may also store weights such as apodization weights and/or Retrospective Transmit Beamforming (RTB) weights.

As explained herein, the beamformer 103 (circuitry) is configured to apply contemporaneously to each receive signal contribution of each transducer element from a reflection point a beamforming focalization delay and a phase shift equalization delay so called RTB delay. The said beamforming focalization delay being calculated basing on the time of arrival of the said signal contribution to a transducer element when traveling from the reflection point to the said transducer element and the said phase shift equalization delay being determined according to the difference in phase of the wave front reaching the reflecting point relatively to the phase of the wave fronts reaching the same reflecting point and being of further transmitted beams which are laterally shifted each other.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally the memory 105 may store a pre-calculated table, where the pre-calculated table comprises pre-calculated phase shift equalization delays to be applied contemporaneously to the beamforming focalization delays to the receive signals of a receive line along a certain line of sight or a certain receive line position deriving from a certain number of transmit beams being differently laterally shifted relatively to the said receive line position, the number of the said transmit beams being set by setting a certain aperture or lateral width of the said transmit beams. Optionally the memory 105 may store a pre-calculated table of the said phase shift equalization delays which are pre-calculated for one or more of different transmit beams apertures or widths.

Optionally, the processor 106 may be configured to calculate the said phase shift equalization delays for one or more of different transmit beams apertures or widths.

Optionally, the beamformer 103 circuitry may further comprise an adder unit for adding the beamforming delays and the phase shift equalization delays (RTB delays) for the receive signal contributions deriving from each reflecting point.

In accordance with certain embodiments, at least a portion of the beamforming process may be implemented by the processor 106 (e.g., in connection with software RTB beamforming). For example, the memory 105 may store beamforming related program instructions that are implemented by the processor 106 to contemporaneously apply beamforming delays and phase shift equalization delays to the receive signals.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user input data interface 114 and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

According to an embodiment the ultrasound system of FIG. 1 is provided with a Positioning, steering angle and correction angle processor indicated with 161. This processor is configured to determine in an automatic way the best position relative to a vessel or a flux in the target region of the region of interest (ROI) of the color Doppler flow or the best position of the Doppler sample gate. Furthermore the processor 161 calculates the best steering angle of the transmit beams for acquiring Doppler signals and data and the best Doppler correction angle.

Figure 3:
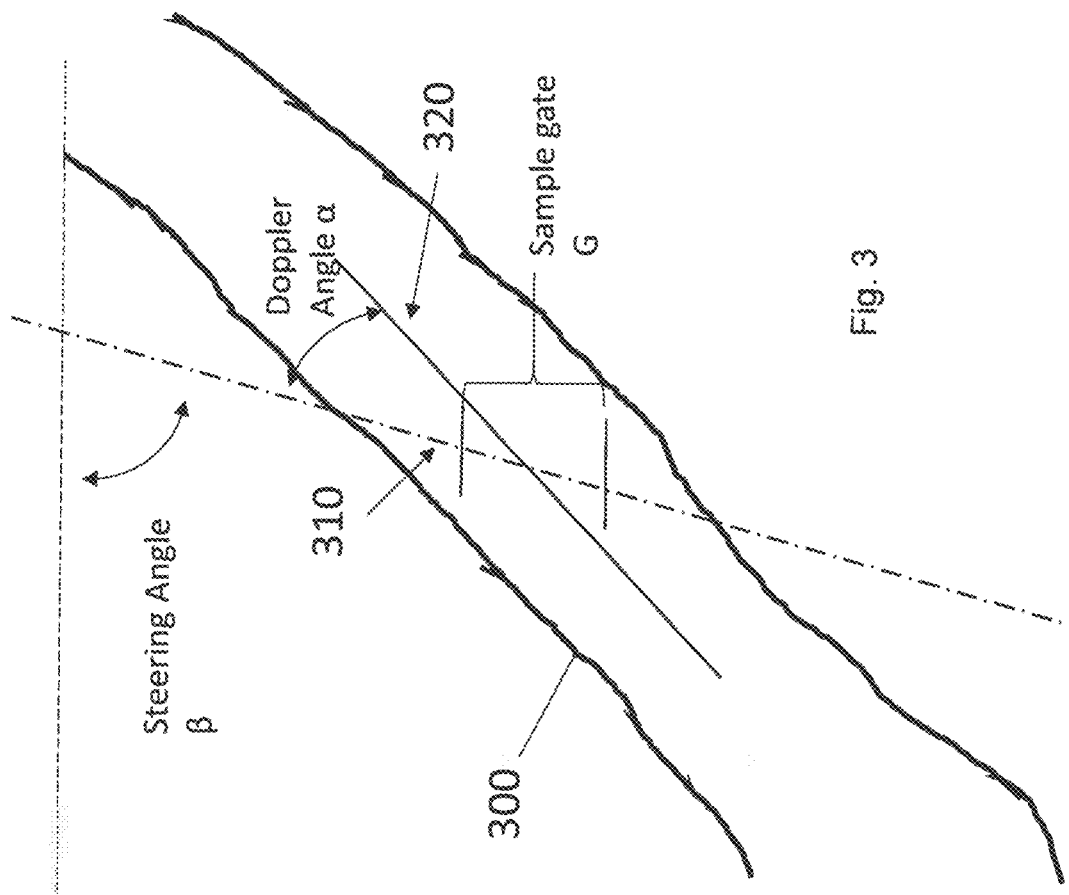
FIG. 3 illustrates diagrammatically a blood vessel the beam direction, the flow direction and the sample gate.

FIG. 3 shows a schematic representation of a target region in which a vessel 300 is present containing a flow. With 310 the beam direction is indicated which is at an angle of the unsteered beam propagation direction of a transmit beam generated by a probe and which in general is essentially perpendicular to the surface of the transducer array in the case of a plane array or perpendicular to a tangent surface to the curved surface of a curved array. The steering angle β is indicated in the representation of FIG. 3 as well as the correction angle α, which is the angle between the direction of the flow indicated by 320 and the steered transmit beam direction or propagation axis 310.

Since Doppler data is based on phase shifts between the transmit beam and the reflected beam due to motion, the motion has to have at least a component parallel to the transmit beam otherwise there will be no Doppler contribution in the reflected beam. As it appears clearly the correct positioning of the ROI or sample gate G and the determination of the best steering angle and correction angle will be essential to the quality of the Doppler data and thus to obtain best possible color Doppler information of the flow.

In the embodiment of FIG. 1 the processor 161 receives color Doppler signals from the Color Doppler processor CFM and determines a morphological feature of the flows and the corresponding vessels in the target region. Based on this feature the processor calculates automatically the best positioning of the ROI and/or of the sample gate and the best steering angle of the ultrasound beam and the correction angle. The best positioning of the ROI is determined by finding the pixels in an image corresponding to the color Doppler signals a maximum value of image pixels. The position of this pixel or of these pixels is set as the position of the ROI or sample gate. This information is sent to the CFM processor or to the CPU 112 for operating the ROI positioning in the displayed image according to the structure of the system as described above.

For determining the best steering angle of the ultrasound beam and/or the best correction angle the processor applies, at the position of the pixel or pixels having a maximum value as determined in the previous step and in the image reproducing the color Doppler signals or data, four directional filters set according to four different directions. The output of the filters is then combined for generating components of a vector whose direction is the direction of the flow. The processor 161 also determines as a function of the output signals of the four direction filters a quality factor which corresponds to a normalized modulus of the vector and which is a measure for evaluating the quality of the flow direction determined by the vector.

Figure 4:
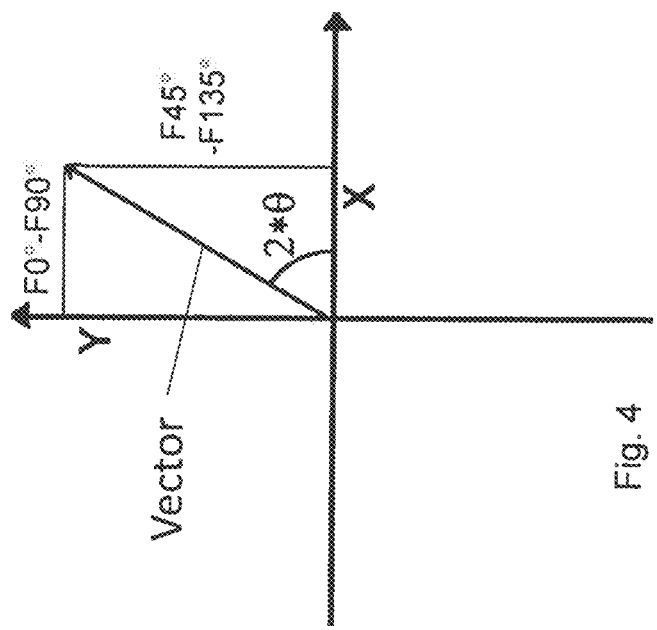
FIG. 4 illustrates a coordinate system in which the components of the vector combining the output data of the direction filters is graphically described.

This situation is shown in FIG. 4 and will be described later with greater detail.

The steering angle and the correction angle are determined by the processor as a function of the determined direction of flow if the quality factor is above a certain threshold which can be set by the user and or by the producer and installer of the system and which can be based on empirical data acquired in a setting and tuning process.

Figure 2:
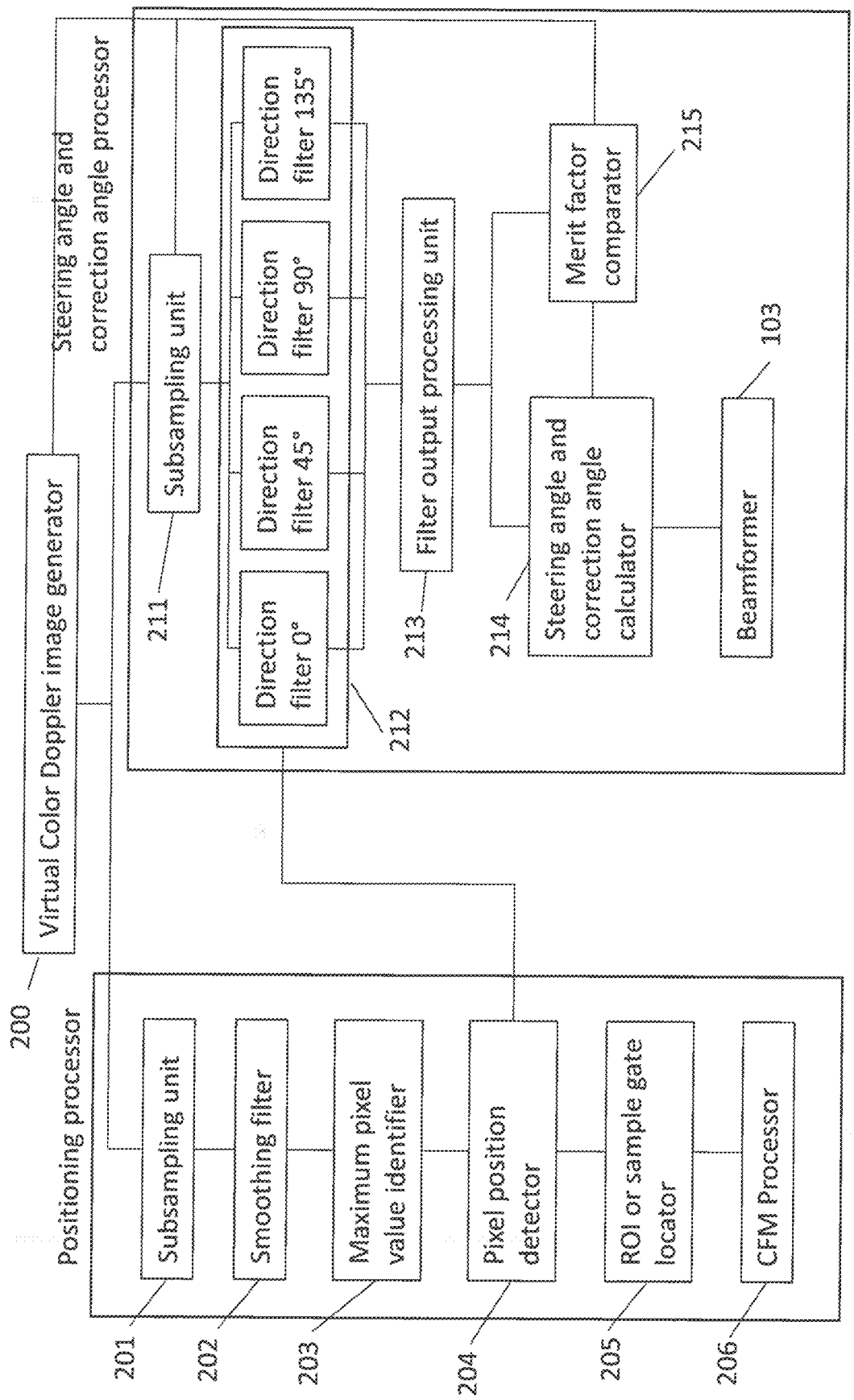
FIG. 2 illustrates a block diagram of an embodiment of a Positioning processor and a Steering Angle and Correction angle processor.

FIG. 2 shows a block diagram of an embodiment of the Positioning, Steering Angle and Correction Angle Processor 161. According to the principles of this embodiment, the calculation of the best position of the color Doppler ROI and or of the sample gate G are carried out on image data. This image data may consist in a virtual Doppler image constructed by a dedicated processor or can be obtained from the power output of the CFM processor for example according the system architecture of FIG. 1. This virtual image generator 200 of FIG. 2 is to be interpreted as comprising both variants. The positioning processor comprises a subsampling unit 201 which is configured to subsample the virtual image, as for example by a factor 2. The subsampled image is further processed by a smoothing filter 202 and the filtered image is processed by a maximum value identifier 203 and by a pixel position detector 204 which registers the position of the pixels having the maximum value. This positional data is saved and is used by a ROI and sample gate locator 205 producing data of the ROI and sample gate position to be provided to the image generating chain such as for example to a CFM processor interface 206 which provides communication to a CFM processor as for example the one shown in FIG. 1. The information of the position in the virtual image of the pixel having a maximum value are furnished to the Steering angle and correction angle processor shown in FIG. 2. This processor operates also on the virtual image provided by the virtual image generator 200 and after having submitted the image to a subsampling at a factor 2 or higher or different than 2 by the subsampling unit 211, applies to the subsampled image data four different directional filters 212, each one set on a different direction. The directions are set according to a sequence of different directions in which each direction is changed by an angular displacement of 45° relatively to the preceding one. The directional filters 212 are centered at the position in the image corresponding to the position of the pixel having the maximum value as determined by the positioning processor. The output of the directional filters indicated in common by the filters 212 is processed by a processing unit 213 which is configured in order to execute an algorithm for determining the directional data of the flow and a quality factor of the said directional data based on which the steering angle and the correction angle are set.

A steering angle calculator 214 calculates the best steering angle and the best correction angle out of the flow direction and is controlled by the output of a merit factor comparator 215 which compares the said quality factor with a threshold and triggers the calculation of the steering angle and of the correction angle as a function of the flow direction only if the merit factor is above the threshold. If this is not the case the process is repeated. This new cycle can be started from the very beginning i.e. by calculating again the position of the maximum pixel value in the image or by restarting the process of subsampling, directional filtering and calculating the flow direction within the steering angle and correction angle processor.

When repeating the cycle by starting from any of the two starting steps indicated above the new cycle can be carried out by changing at least one of the parameters of the process, for example by changing the subsampling factor or the settings of the smoothing filter.

According to a variant embodiment, if after a certain pre-set numbers of repetitions of the cycle the merit factor remains still below the defined threshold value, the process is stopped and the flow direction related to one of the computed merit factors is used as the flow direction based on which the steering angle and the correction angle are determined.

Different variants are possible for choosing the flow direction in the above condition. According to a first variant the flow direction is chosen which corresponds to the merit factor coming closer to the threshold value. In a further variant the flow direction is calculated as a mean value of the different flow directions resulting from each repetition cycle. In this case a weighted mean can calculated using the merit factor for each of the flow directions for determining a corresponding weight. In an embodiment, the weight associated to each flow direction is calculated as a function of the difference of the merit factor corresponding to the flow direction and the threshold value. This function can be linear or non-linear in order to penalize more the flow directions for which the difference between the corresponding merit factor and the threshold value is higher in respect to the flow directions for which the difference between the corresponding merit factor and the threshold value is lower.

The steering angle and the correction angle data are provided to the beamformer 103 for being applied to the transmitted beam.

As already indicated above in relation to the embodiment of FIG. 1, the positioning processor and the steering angle and correction angle processor can be at least in part (as defined by various functional blocks) implemented with dedicated hardware, analog and/or digital circuitry, and/or one or more processors operating program instructions stored in memory. Additionally, or alternatively, all or portions of the processors may be implemented utilizing digital components, digital signal processors (DSPs) and/or field programmable gate arrays (FPGAs) and the like. The blocks/modules illustrated in FIG. 2 can be implemented with dedicated hardware (DPSs, FPGAs, memories) and/or in software with one or more processors.

Directional filters can be designed for any direction within a given space. For images, x- and y-directional filters are commonly used to compute derivatives in their respective directions. The following array is an example of a 3 by 3 kernel for an x-directional filter (the kernel for the y-direction is the transpose of this kernel):

$$\begin{bmatrix} -1 & 0 & 1 \\ -1 & 0 & 1 \\ -1 & 0 & 1 \end{bmatrix}$$

Figure 5:
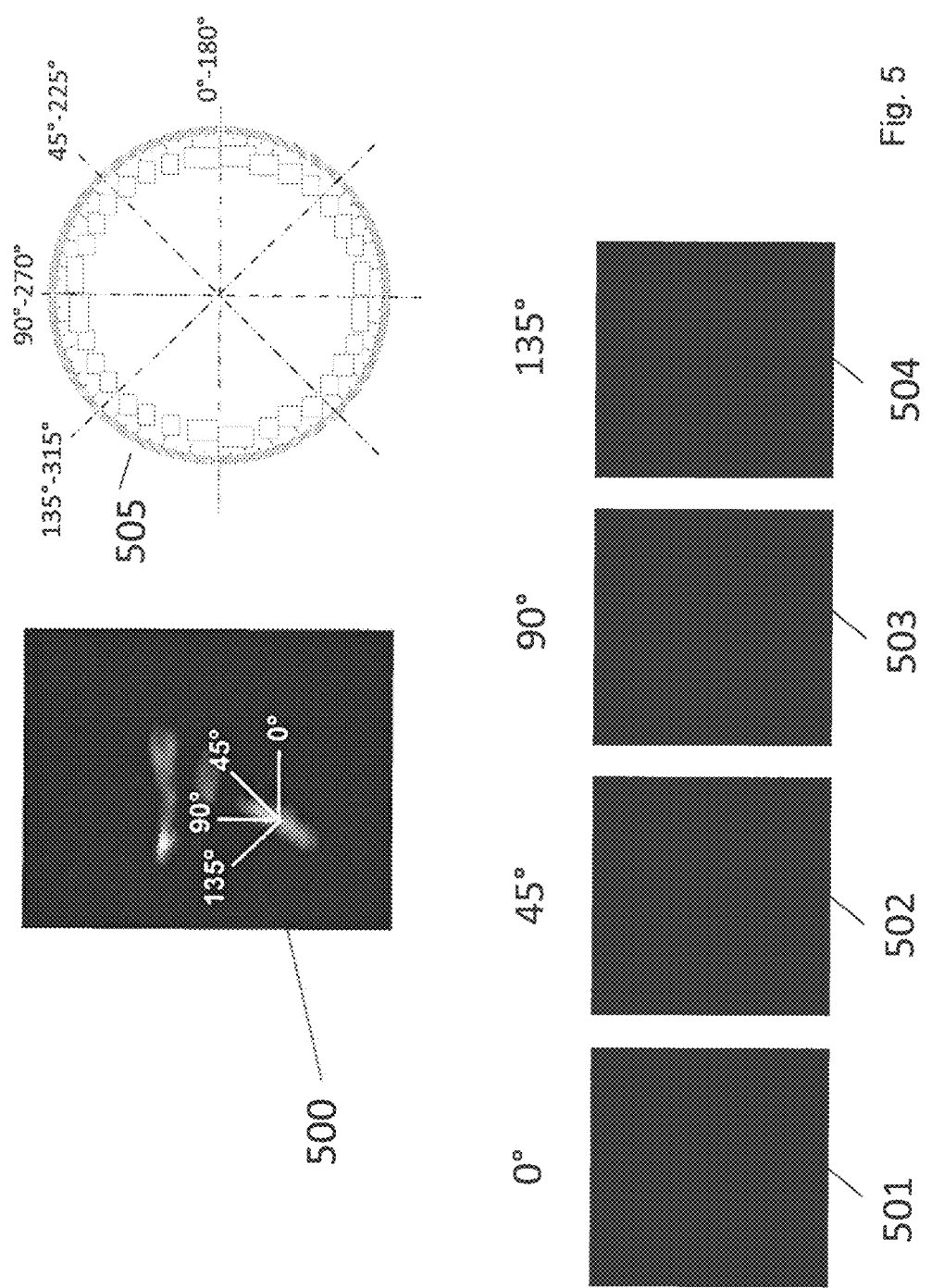
FIG. 5 illustrates output images of the effect of each direction filter on the image of a flow.

The above array is an example of one possible kernel for a x-directional filter. Other filters may include more weighting in the centre of the nonzero columns. Directional filters as well as an example code is described at northstar-www.dartmouth.edu/doc/idl/html_6.2/Filtering_an_Imagehvr.html FIG. 5 shows examples of the placing of the directional filters at the maximum value position on the subsampled color Doppler image 500 and the directions at which the four filters are set. A goniometer 505 shows the direction definition notation utilized in the description and in the claims. The directions briefly indicated by 0°, 45°, 90°, 135° in the image representation 500, are defined by goniometer with axis connecting two angular positions so the notation 0° corresponds to the direction of the axis 0°-180°, 45° corresponds to the axis and direction 45°-225°, 90° to the axis 90°-270° and 135° to the axis 135°-315°. The goniometer being aligned with the direction of a reference coordinate system with orthogonal axis.

The FIGS. 501 to 504 in FIG. 5 show the graphical representation of the effect of each of the four directional filters.

Figure 6:
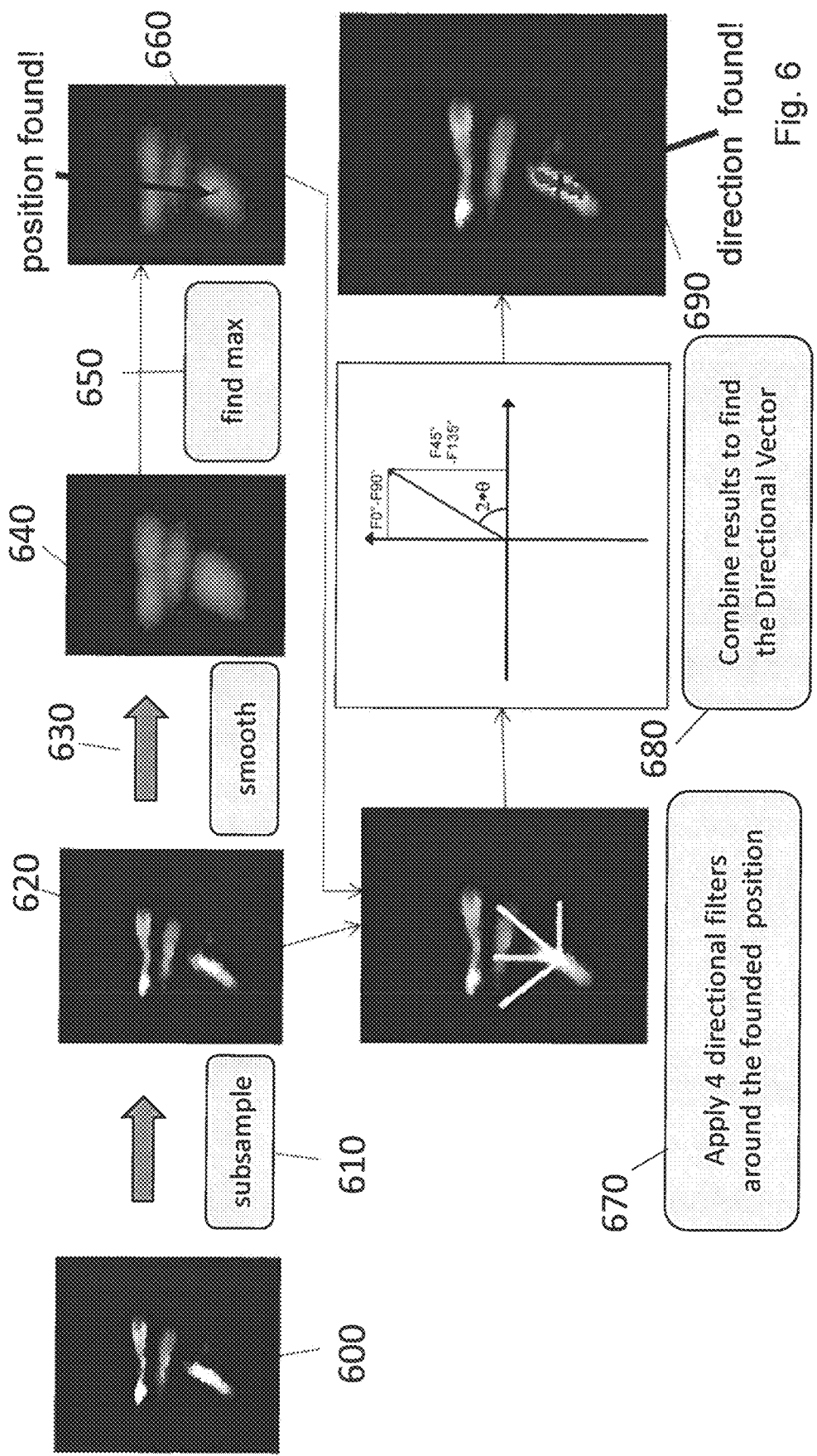
FIG. 6 is a flux diagram illustrating the steps of the method for automatically positioning the color Doppler ROI and/or the sample gate and for automatically determining the steering angle and the correction angle.

FIG. 6 shows a flow diagram of the method for determining automatically the best positioning of the color Doppler ROI and/or of the sample gate G and for selecting the best color Doppler beam direction steering angle and setting the Doppler correction angle.

At step 600 a color Doppler flow image is generated from the color Doppler flow signals. These image data is subsampled at step 610.

According to a preferred embodiment subsampling is carried out by a factor 2. At step 630, the subsampled image 620 is subjected to a filtering by a smoothing filter. The filtered image 640 is then submitted to a searching algorithm at step 650 for finding the maximum pixel or pixels value and identifying its position as indicated by the image 660 by the arrow.

This position is the position to be used for positioning the ROI and/or the sample gate. Furthermore, this position is the position at which the directional filters has to be positioned, as will be described.

Starting from the sampled image 620, at step 670 the four directional filters are applied to the image being positioned at the pixel position corresponding to the max value. At step 680 the outputs of the directional filters are combined for calculating the direction and a merit factor of the calculated direction in order to determine if the calculated direction is reliable or not and if it can be used as a reference direction for setting the steering angle of the beam direction and the Doppler correction angle. At step 690 the direction of the flow resulting from the combination of the filter outputs at step 680 is shown and indicated by the arrow.

Defining the output of the four directional filters with F0 for the direction 0°-180°, F45 for the direction 45°-225°, F90 for the direction 90°-270° and F135 for the direction 135°-315°, the direction of flow is computed from the phase of a vector having components x and y as indicated in FIG. 4 and in which the component x is computed as the difference of the outputs of the filters aligned along the directions 0°-180° and 90°-270°:

$$X = F0 - F90;$$

Similarly, the component y is computed as the difference of the outputs of the filters aligned along the directions 45°-215° and 135°-315°:

$$Y = F45 - F135.$$

The phase is computer according to the following function:

$$\text{DIRECTION} = \frac{1}{2}\text{atan}\left(\frac{Y}{X}\right)\frac{180}{\pi}$$

The merit factor is computed according to the following function which corresponds to the definition of a normalized modulus of the vector with the component X,Y:

$$Q = \frac{\sqrt{(F0 - F90)^2 + (F45 - F135)^2}}{\sqrt{(F0 + F90)^2 + (F45 + F135)^2}}$$

This value is used in combination with a threshold for determining the reliability of the estimation. If comparing the computed merit factor Q this value is above the threshold, the estimated flow direction is considered reliable and is used for determining the steering angle and the correction angle. If the merit factor is below the threshold, the direction estimation is not reliable and the process is repeated for computing a new flow direction.

The repetitions can be carried out according to one or more of the different variants and embodiments described above in relation to FIG. 2.

Figure 7:
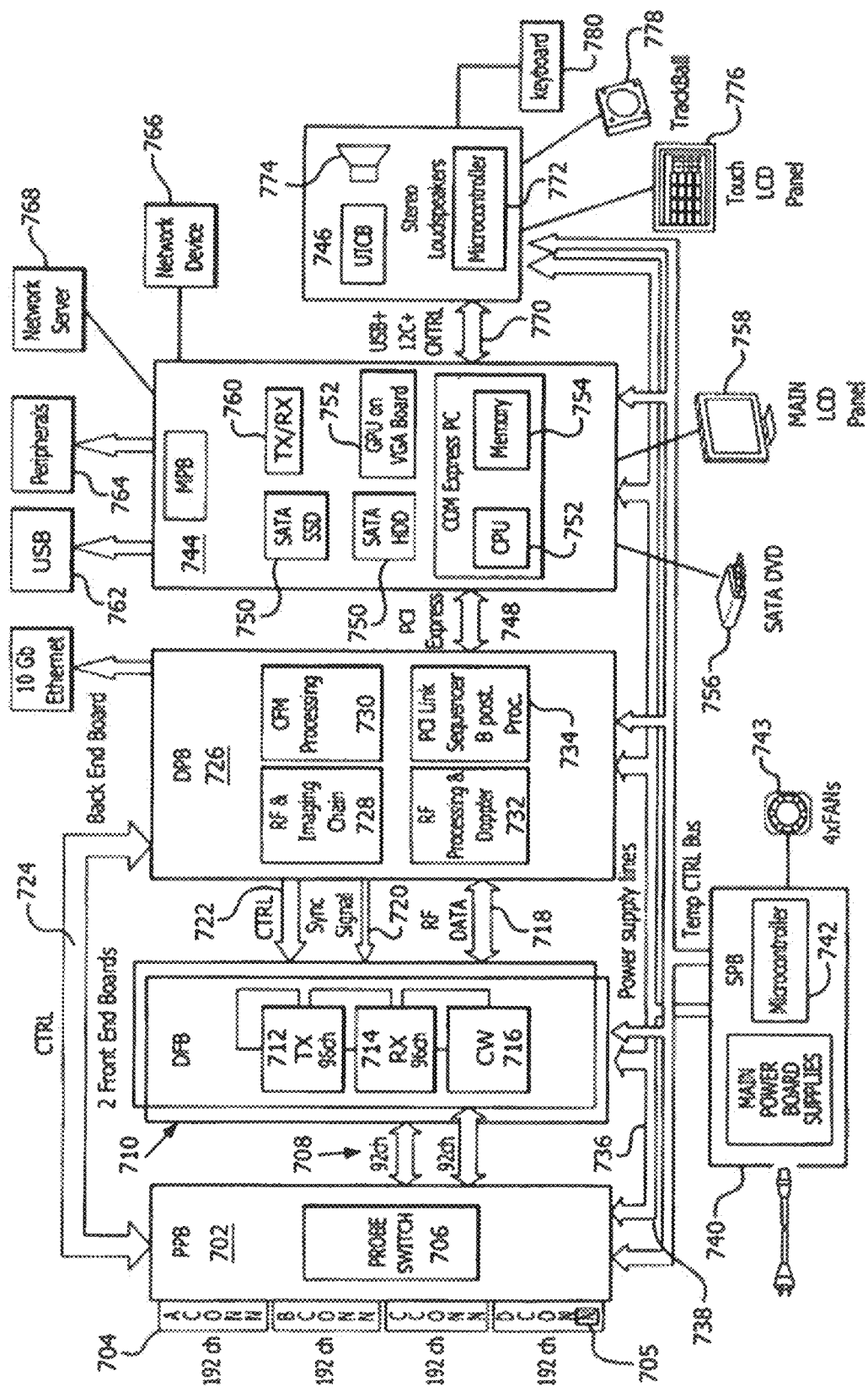
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 726. A power supply line 736 provides power from a power supply 740 to the various components of the system, including but not limited to, the probe interconnection board (PIB) 702, digital front end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a Peripheral Component Interconnect (PCI) link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial Advanced Technology Attachment (ATA) solid-state devices, serial ATA hard disk drives, etc.), a visual graphics array (VGA) board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the liquid crystal display (LCD) touch panel 776, as well as collecting user inputs via the touch panel 776, trackball 778 and keyboard 780, where such user inputs are conveyed to the master processing board 744 in connection with implementing embodiments herein.

Figure 8:
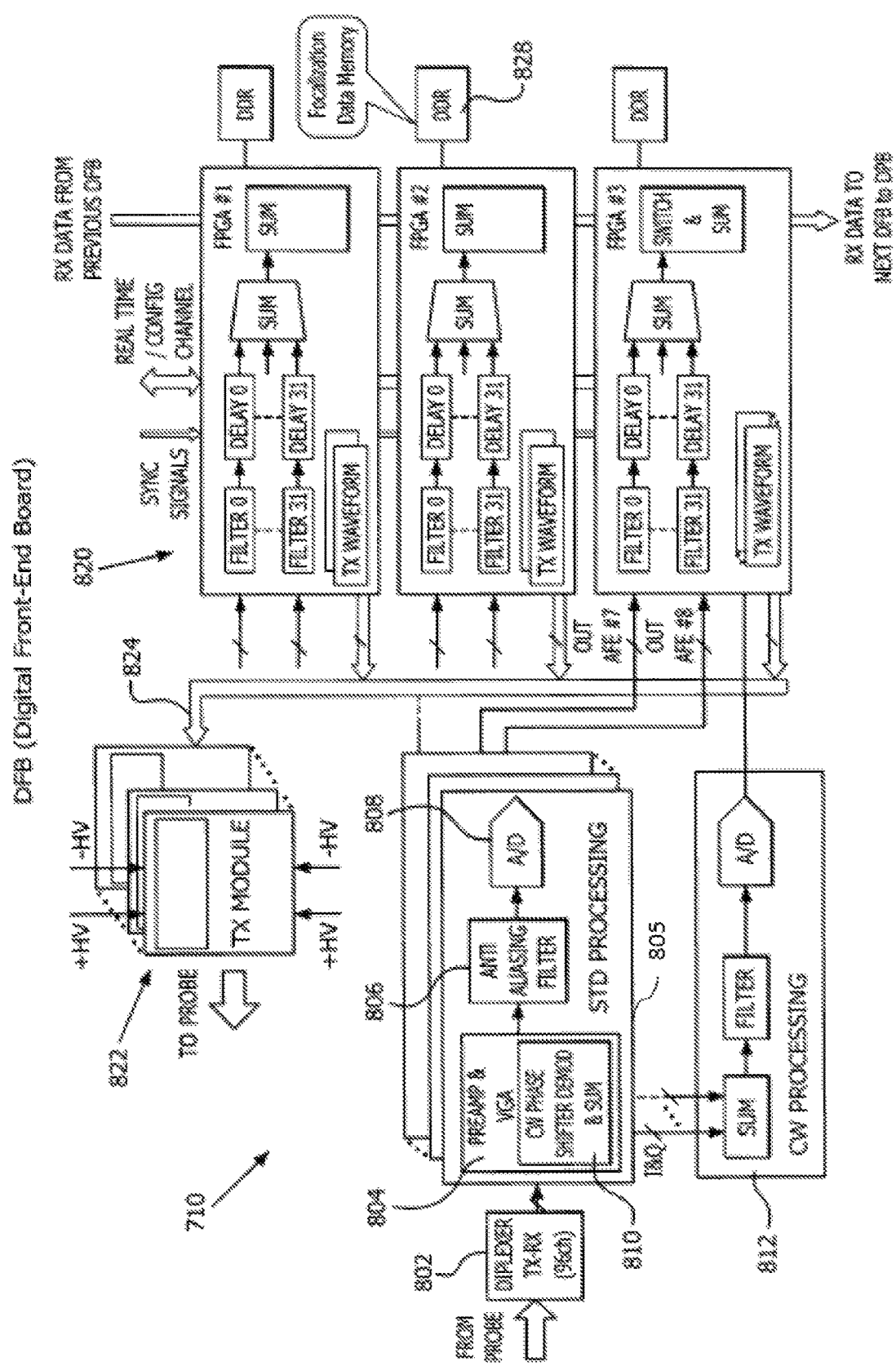
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment, the retrospective transmit beam focusing may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 726 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 744 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 744 provides real-time configuration information and synchronization signals in connection with each channel to the digital front-end board 710.

It should be clearly understood that the various arrangements and processes broadly described and illustrated with respect to the FIGS. 1-9, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS. 1-9, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for real time automatic setting of parameters for Doppler mode or color Doppler imaging mode comprising:
   transmitting ultrasound beams in a target body and receiving the reflected beam from said target body;
   extracting Doppler signals from said reflected beam;
   processing the Doppler signals to identify an area where the Doppler signals indicate that a flow is present and processing the Doppler signals relating to the said area for automatically determining one or more of the following parameter settings:
   positioning of the color Doppler region of interest (ROI) and/or of the Doppler sample Gate, determining and applying a color Doppler beam steering angle, setting the Doppler correction angle,
   wherein processing the said Doppler signals comprises:
   analyzing the shape of the identified Doppler area by processing the corresponding Doppler signals for determining:
   a) the position of a flow having the most significant intensity;
   b) the direction of the flow at the position referred in a);
      determining the position of the color Doppler ROI and/or of the Doppler sample gate as a function of the said position of the flow having the most significant intensity and positioning the said color Doppler ROI and/or sample gate on that position;
      determining the steering angle of the transmit beams and/or the Doppler correction angle as a function of the direction of the flow at the position of a flow having the most significant intensity.

2. Method according to claim 1 wherein analyzing the shape of the identified Doppler area is based on morphological features of the flow determined from the Doppler flow signals.

3. Method according to claim 1, wherein analyzing the shape of the identified Doppler area comprises creating a Doppler image of the flow from the Doppler signals.

4. Method according to claim 3, wherein determining the position of a flow having the most significant intensity comprises:
calculating the maximum value of the pixels or voxels of the Doppler image and selecting the position of the said pixel or voxel as the position of the flow.

5. Method according to claim 3, wherein determining the direction of the flow comprises:
applying four directional filters on the Doppler image at the position of the pixels having the maximum value, the said directional filters being oriented respectively along one of four directions each being rotated of 45° with respect to an adjacent direction;
combining the output of the said four directional filters to obtain a vector;
determining the flow direction as a function of the direction of said vector.

6. Method according to claim 3, wherein determining the direction of the flow comprises:
applying four directional filters on the Doppler image at the position of the pixels having the maximum value, the said directional filters being oriented respectively along the following directions defined by the axis passing through the directions of a goniometer centered on the center position of the flow according to the following notation 0°-180°, 45°-215°, 90°-270° and 135°-315° the goniometer being aligned with the axis of a Cartesian system defining the two dimensions of the image with the 0°-180° axis and the 90°-270° axis;
combining the output of the said four directional filters forming a vector with orthogonal components x and y having the following values X=(output of the filter having direction 0°-180°)–(output of the filter having direction 90°-270°) and Y=(output of the filter having direction 45°-215°)–(output of the filter having direction 135°-315°);
determining the phase of the vector and calculating the flow direction angle as a function of the said phase.

7. Method according to claim 3, wherein the Doppler image is subsampled.

8. Method according to claim 3, wherein the Doppler image is filtered by a smoothing filter.

9. Method according to claim 6, wherein the flow direction angle is calculated as:

$$\text{DIRECTION} = \frac{1}{2}\text{atan}\left(\frac{Y}{X}\right)\frac{180}{\pi}$$

10. Method according to claim 6, wherein the normalized module Q of the vector is calculated and used as a quality factor of the estimated direction.

11. Method according to claim 10, wherein the normalized module Q of the vector is calculated as:

$$Q = \frac{\sqrt{(F0-F90)^2 + (F45-F135)^2}}{\sqrt{(F0+F90)^2 + (F45+F135)^2}}$$

where:
F0 is the output of the filter having direction 0°-180°;
F45 is the output of the filter having direction 45°-215°;
F90 is the output of the filter having direction 90°-270° and
F135 is the output of the filter having direction 135°-315°.

12. Method according to claim 10 further comprising:
defining a threshold for the value of the normalized module;
calculating the said normalized module Q;
comparing the said calculated value for the normalized module with the threshold;
setting the Color Doppler Beam-axis steering angle and the Doppler correction angle according to the flow directions calculated as the function of the phase of the same vector of which the normalized module is calculated if this calculated value of the said normalized module is above the threshold.

13. An ultrasound imaging system for real time automatic setting of parameters for Doppler modes comprising:
an ultrasonic probe including a transducer array which probe transmits ultrasound beams in a target region where a flow is present and which receives the echo signals reflected by the said target region;
a beamformer;
a Doppler processor producing Doppler signals from the echo signals;
an image processor producing Doppler images of the flows in the target region;
a Color Doppler ROI and/or Doppler sample gate positioning processor for automatically positioning the ROI and/or a sample gate in the position relative to the imaged flow;
a Steering angle and/or Doppler correction angle processor for automatically determining the steering angle and setting the corresponding correction angle of the ultrasound beams propagation directions;
wherein
the said Color Doppler ROI and/or Doppler sample gate positioning processor and the steering angle and/or Doppler correction angle processor are configured to:
process the color Doppler flow signals;
determine data relating to morphological features of the flow at the position of the flow having the most significant intensity; and
calculate the position for the Color Doppler ROI and/or the Doppler sample gate as corresponding to that position of the flow having the most significant intensity and, calculate the Steering angle and/or the Doppler correction angle as a function of the said data on the morphological features.

14. An ultrasound imaging system according to claim 13, wherein the positioning processor is provided in combination with a color Doppler image generator generating an image from the color Doppler signals, which positioning processor is configured to determine the maximum pixel value and the position of the corresponding pixel, wherein the positioning processor comprises a ROI or sample gate locator automatically positioning or centering the ROI and/or the sample gate at the position of said pixel having the maximum value.

15. An ultrasound imaging system according to claim 13, wherein the Steering angle and/or Doppler correction angle processor is provided in combination with a color Doppler image generator generating an image from the color Doppler signals and comprises four direction filters each oriented along one of four directions each being rotated of 45° with respect to an adjacent direction to which the image is provided, the outputs of the four directional filters being provided in input to the Steering angle and/or Doppler correction angle processor to calculate the flow direction and a quality factor of the calculated direction.

16. An ultrasound imaging system according to claim 15, wherein the Steering angle and/or Doppler correction angle processor is configured to calculate the flow direction angle as:

$$\text{DIRECTION} = \frac{1}{2}\text{atan}\left(\frac{Y}{X}\right)\frac{180}{\pi}$$

17. An ultrasound imaging system according to claim 15, wherein the Steering angle and/or Doppler correction angle processor is configured to calculate the normalized module Q of the vector, to be used as a quality factor of the estimated direction, as:

$$Q = \frac{\sqrt{(F0 - F90)^2 + (F45 - F135)^2}}{\sqrt{(F0 + F90)^2 + (F45 + F135)^2}}$$

where:
F0 is the output of the filter having direction 0°-180°;
F45 is the output of the filter having direction 45°-215°;
F90 is the output of the filter having direction 90°-270° and
F135 is the output of the filter having direction 135°-315°.

18. An ultrasound imaging system according to claim 14, the positioning processor further comprising a subsampling unit for subsampling the Color Doppler image and a filter for smoothing the subsampled image.

19. An ultrasound imaging system according to claim 17, wherein the Steering angle and/or Doppler correction angle processor comprises a memory for saving a threshold value for the quality factor and a comparator for comparing the calculated quality factor with the threshold, the comparator output being read by the Steering angle and/or Doppler correction angle processor for determining whether the flow direction calculated can be used for determining the steering angle of the transmit beam and/or the Doppler correction angle.

20. Non-transitory readable medium characterized in that on the said medium the instructions are coded for configuring a generic processor and optionally the peripherals connected to it in such a way that the processor and one or more of the said peripherals carry out the functions needed for executing the method according to claim 1, the said medium being readable by a storage media reader or being stably installed as a peripheral of the processor.

21. An ultrasound imaging system according to claim 15, the Steering angle and/or Doppler correction angle processor further comprising a subsampling unit for subsampling the image prior to input to the four direction filters.

* * * * *